(12) United States Patent
Nybom

(10) Patent No.: US 7,090,718 B2
(45) Date of Patent: Aug. 15, 2006

(54) DEVICE FOR COLLECTING CHARGED PARTICLES WITH THE AID OF AN IONIZER FOR PURPOSES OF ANALYSIS

(76) Inventor: Rolf Nybom, Bör jesons väg 42 SE-161 55, Bromma (SE)

( * ) Notice: Subject to any disclaimer, the term of this patent is extended or adjusted under 35 U.S.C. 154(b) by 430 days.

(21) Appl. No.: 10/399,304

(22) PCT Filed: Oct. 26, 2001

(86) PCT No.: PCT/SE01/02353

§ 371 (c)(1),
(2), (4) Date: Apr. 15, 2003

(87) PCT Pub. No.: WO02/35209

PCT Pub. Date: May 2, 2002

(65) Prior Publication Data

US 2004/0014139 A1    Jan. 22, 2004

(30) Foreign Application Priority Data

Oct. 27, 2000  (SE) .................................... 0003913

(51) Int. Cl.
*B03C 3/40* (2006.01)
(52) U.S. Cl. ...................... 96/94; 96/95; 96/98; 96/413
(58) Field of Classification Search ............. 96/94–98, 96/413, 18, 19, 25, 26
See application file for complete search history.

(56) References Cited

U.S. PATENT DOCUMENTS

| | | | |
|---|---|---|---|
| 3,879,986 A * | 4/1975 | Sehmel | 73/28.04 |
| 3,957,374 A * | 5/1976 | Kriese et al. | 356/312 |
| 4,976,752 A * | 12/1990 | Torok et al. | 96/43 |
| 5,254,861 A | 10/1993 | Carpenter et al. | |
| 5,538,692 A * | 7/1996 | Joannou | 422/121 |
| 5,814,135 A * | 9/1998 | Weinberg | 96/58 |
| 5,837,035 A * | 11/1998 | Braun et al. | 95/78 |
| 6,077,334 A * | 6/2000 | Joannou | 96/66 |
| 6,126,727 A * | 10/2000 | Lo | 96/39 |
| 6,508,982 B1 * | 1/2003 | Shoji | 422/22 |

FOREIGN PATENT DOCUMENTS

EP           321419    *   6/1989   ...................... 96/98

* cited by examiner

*Primary Examiner*—Richard L. Chiesa
(74) *Attorney, Agent, or Firm*—Frishkauf, Holtz, Goodman & Chick, P.C.

(57) ABSTRACT

A device is provided for collecting particles from a gas for subsequent analysis with a particle analyzer. The device includes an ionizer with at least one ion-emitting unit which emits ions and a collector for collecting particles charged by the ions. An electrically conductive capturing or collecting device is electrically connected to the collector of the ionizer.

22 Claims, 2 Drawing Sheets

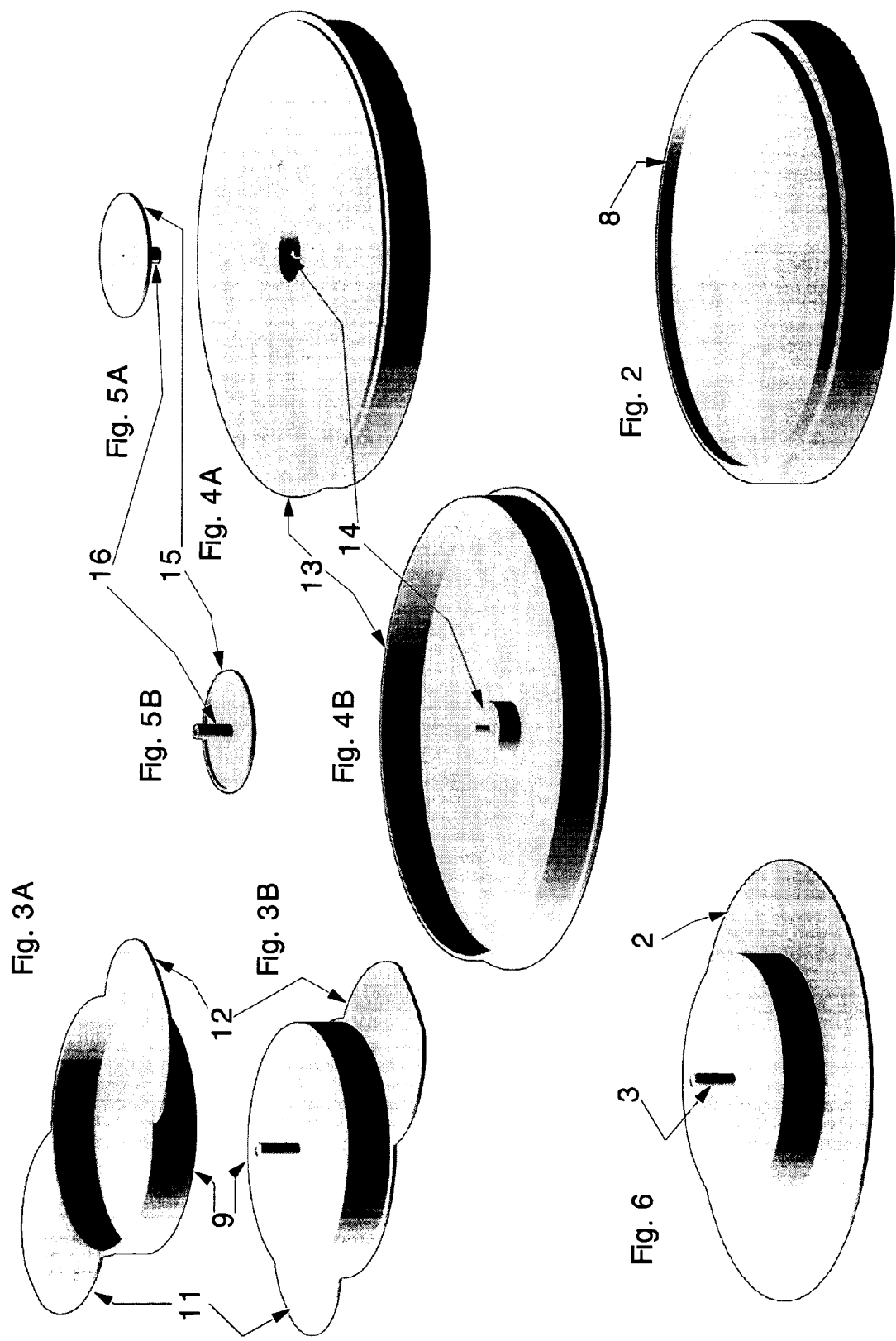

DEVICE FOR COLLECTING CHARGED PARTICLES WITH THE AID OF AN IONIZER FOR PURPOSES OF ANALYSIS

This application is a U.S. National Phase Application under 35 USC 371 of International Application PCT/SE01/02353 filed Oct. 26, 2001.

OBJECT OF THE INVENTION

The present invention relates to a device for collecting, with the aid of an ionizer which emits ions and which is equipped with a collector for collection of charged particles, particles from air or from some other gas charged by means of the said ions. These collected or captured particles are intended for subsequent analysis in a particle analyzer established for this purpose.

TECHNICAL FIELD

As a rule it is difficult to collect or capture, from air or other gases, minute particles such as mould spores, bacteria, viruses, dust, pollen, smoke, plant parts, fungus spores, allergens, particles from animals etc.

With the aid of an ionizer, i.e. an apparatus which generates and sends out or emits to the air electrically charged ions, and especially if the said ionizer is also equipped with a collector which provides an opposite polarity to that of the said ions, these electrically charged ions will adhere to minute particles present in the air and the said thus electrically charged particles will thereby endeavour to be collected on the said collector. The few particles that as a rule are present in the air will be concentrated to the collector through the effect of the electrostatic field. These collected or clustered particles can subsequently be removed from the collector, for example by scraping off, and introduced into a suitable analyzer, for example a scanning electron microscope, for more detailed analysis, for example determination of the size, amount and nature of the particles.

The method outlined above has proved to be highly successful in terms of the measuring results attained and subsequent analysis but in itself is not well suited for rational analysis work.

Examples of this are those cases in which it is desirable to carry out continuous measurements and analysis of air over prolonged periods of time in a space, while each individual measurement is to embrace a shorter time, which presupposes that a large number of ionizers will be needed and that each ionizer is submitted for analysis.

A further case by way of example is when it is proposed to analyze the air in each individual room within a building with numerous rooms, for example in order to check the true efficiency of the air exchange in the individual rooms within a building and/or in order to detect any pollution hotbeds (for example accumulations of bacteria) in the ducts of a filter or air-conditioning unit, which case also calls for a large number of ionizers, in fact one for each room, and these ionizers subsequently have to be individually sealed and sent to an analytical laboratory.

In each such analysis the captured particles have to be scraped off or removed in some other suitable manner from the collector of the ionizer prior to analysis and during such removal other particles can be added by mistake without these other particles having been present in the original sample or particles can be removed from the sample, which means that scraping off of particles from the ionizer prior to analysis constitutes a source of error in itself.

In principle this known method is thus neither adapted to nor suitable for sampling on a large scale.

OBJECT OF THE PRESENT INVENTION

The aforesaid disadvantages have been eliminated or have been reduced in the device according to the present invention mentioned in the descriptive preamble in that it incorporates an electrically conductive capturing or collecting device which is disposed electrically connected to the collector of the said ionizer. A particularly advantageous solution according to the present invention is if the said capturing or collecting device is arranged uncoverable, preferably detachable in relation to the collector of the ionizer and if the said capturing or collecting device is designed essentially in the form of a bowl and if the said capturing or collecting device is adapted to and arranged to be covered with a lid after collection has been performed.

BRIEF DESCRIPTION OF THE ACCOMPANYING DRAWINGS

Other embodiments of the invention will become evident from the appended patent claims and from the description hereinbelow of various embodiments, with particular reference to the accompanying drawings, of which FIG. 1 shows a perspective view of an ionizer with a first type of capturing or collecting device, which however is shown somewhat separated from the normal position from the ionizer in order to make clear the design of the collector of the ionizer and of the capturing or collecting device.

FIG. 2 shows a perspective view of a protective cover or lid which is made to fit the first type of capturing or collecting device.

FIG. 3A shows a perspective view of a second type of capturing or collecting device with lugs, which is viewed obliquely from above.

FIG. 3B shows the capturing or collecting device with lugs according to FIG. 3A but viewed from below, FIG. 4A shows a perspective view obliquely from above of a third embodiment of one part of a capturing or collecting device.

FIG. 4B shows the said third embodiment viewed from below.

FIG. 5A shows the remaining part of the said third embodiment viewed obliquely from above.

FIG. 5B shows in a perspective view and viewed from below the remaining part of the said third embodiment, and FIG. 6 shows a perspective view of the first type of the capturing device according to FIG. 1 but viewed from below.

DESCRIPTION OF A PREFERRED EMBODIMENT

Figure 1:
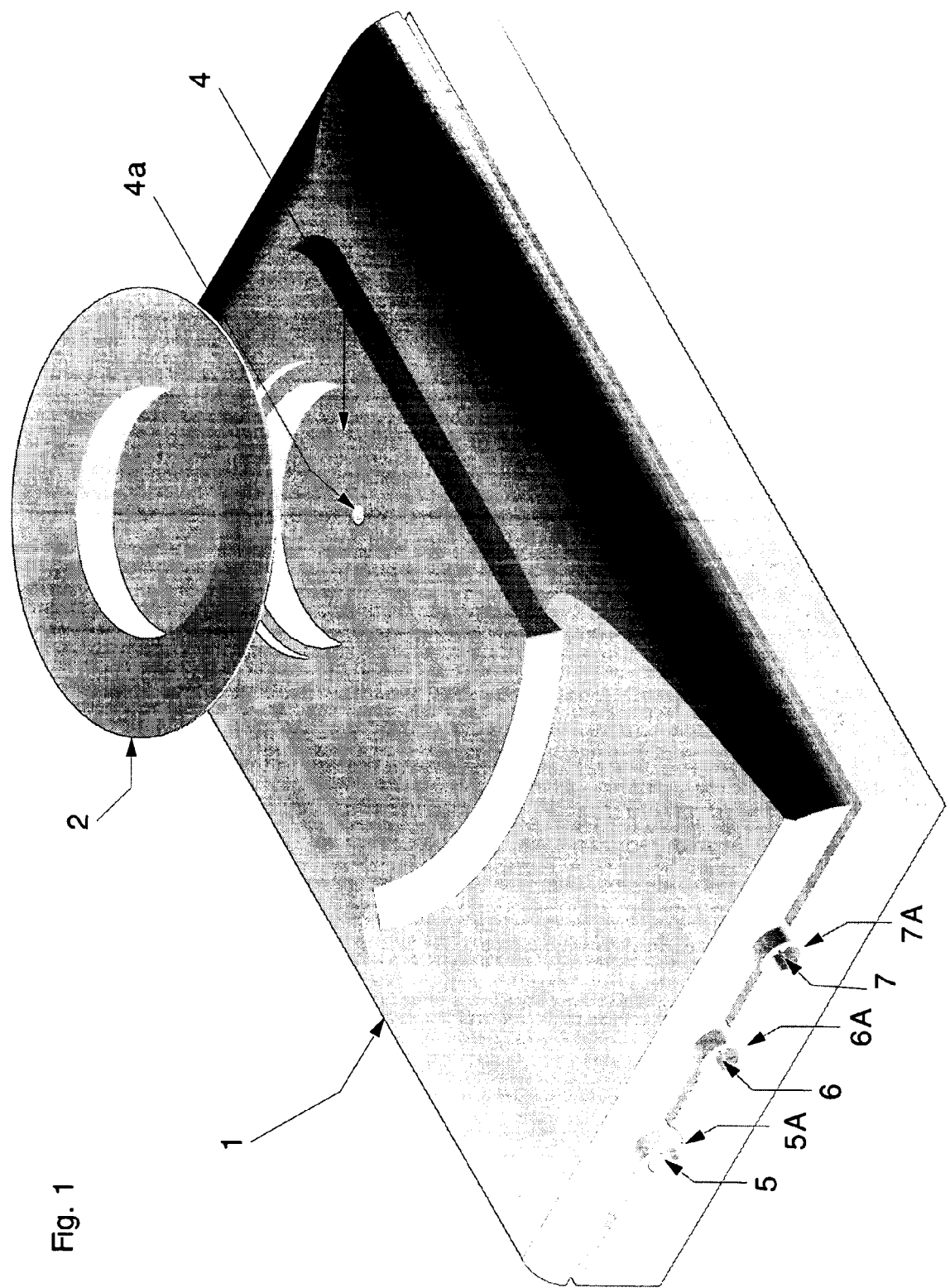

An ionizer 1 according to FIG. 1 comprises a case in which the necessary electric and electronic circuits are housed. The ionizer 1 can be powered by the mains or by a battery as desired. The connections of the electric circuits are not included in the present invention and are per se covered by prior art technique, and for this reason are not described in greater detail here. A number of units 5, 6, 7, preferably emitting negative ions, are located in one end of the said ionizer 1 and are provided with electrically and mechanically protective sleeves 5a, 6a, 7a, which surround and protect the ion-emitting prongs 5, 6, 7. It should be noted in this context that the said prongs 5, 6, 7 are directed away from the ionizer 1 and are located at a long distance from a collector 4 which is built into the ionizer 1 and is given an electric potential opposite to that of the said ion-emitting units 5, 6, 7. It should also be noted that the effective surface of the said collector 4 is relatively large and that in the embodiment shown here is constructed to advantage at least partially submerged in the ionizer 1. Located in the bottom of the collector 4 is a preferably central recess 4a, the primary purpose of which is to steer in and electrically connect the collector 4 with the various collection devices 2, 9, 13, 15, which can be utilized in the collector 4 of the ionizer 1.

The ionizer 1 functions in the following manner. Ions, i.e. electrically charged, preferably negatively charged, particles are emitted from the prongs 5, 6 and 7 in a direction away from the ionizer 1 and especially in a direction away from its collector 4, which has been given an electrical potential which tends to attract the ions emitted from the prongs 5, 6 and 7. the said potential appropriately being positive. Because of this the said ions tend to migrate from the prongs 5, 6 and 7 in a wide arc to the collector 4 through the influence of the electrostatic field generated between the prongs 5, 6 and 7 and the collector 4 and while they are moving the said ions will encounter minute particles in the air. The said minute particles will thereby be charged as well and be caused to follow the electrostatic field in the direction towards the collector 4. Some of these charged particles will reach all the way to the collector 4 where they meet a capturing or collecting device 2 attached to the collector 4, the said device 2 being located in the recess 4a provided in the collector 4 for this purpose. Several particles from the air will gradually be collected on the capturing or collecting device 2 as ions are emitted from the prongs 5, 6 and 7 and form collections or so-called clusters of particles on the capturing or collecting device 2. In addition to collecting particles from the air the said movement of charged particles through the air to the capturing or collecting device 2 also gives rise to some, albeit limited, stirring of the air within a limited space (i.e. a room), a circumstance which results in the inclusion of further particles in the said movement, and for this reason the ionizer 1 has a stirring effect on the air. This stirring effect can in practice quickly—within for example an hour—influence a whole room with an area of approximately 20 square meters to a relatively large extent.

The collector 4 of the ionizer consists of for example an electrically conductive metal or of an electrically conductive plastic, or has been provided with an electrically conductive coating and imparted a surface that is electrically active and which in relation to a capturing or collecting device 2 for particles is advantageously but not necessarily larger than the active surface of the latter. The capturing or collecting device 2 is arranged so that it becomes fixed in position when it is inserted towards the top of the collector 4 into the recess provided for this purpose, for example with the aid of a lug 3 protruding from its back, the said lug 3 being established to interact mechanically and electrically with a narrow recess 4a which is exactly suited in size to the said lug so that a reliable electrical contact is thus established between the collector 4 of the ionizer and the capturing or collecting device 2 while permitting simple removal or detachment of the capturing or collecting device 2 from the collector 4 of the ionizer 1 after the collection task has been completed.

The capturing or collecting device 2 shown in FIG. 1 and FIG. 6 is designed essentially as a bowl with a readily gripped edge protruding beyond for example parts of the collector 4, whereby the capturing or collecting device 2 can easily and smoothly be inserted in the collector 4 of the ionizer 1 and removed from thence without unnecessarily risking affecting in any significant way the particles which have been accumulated on the top side (i.e. the dish-shaped side) of the capturing or collecting device 2 in that essentially only the protruding edge thereof is gripped when moving the capturing or collecting device 2 in relation to the collector 4 of the ionizer 1. To reduce still further the risk of contamination the capturing or collecting device 2, after the collection of particles has been performed but before removal from the collector 4 of the ionizer 1, can be furnished with a lid 8 (see FIG. 2) which exactly fits the capturing or collecting device 2 and which is designed to be snapped round the edge of the capturing or collecting device 2 and remain thus secured during removal of the capturing or collecting device 2 from the collector 4 of the ionizer 1 and during further transport to an analytical instrument, for example an electron microscope or some other suitable instrument which can be located in a completely different place and a long way away from the place where the ionizer 1 has been placed for performance of the investigation in question.

Shown in FIGS. 3A and 3B is a second embodiment of the capturing or collecting device of the ionizer 1. This second embodiment incorporates lugs 11, 12 which protrude from the capturing or collecting device to such an extent that they are easy to grip in relation to the collector 4 of the ionizer 1. A suitably adapted lid, not shown, can—if so desired or required—also be utilized in this case to protect the collected particles and prevent contamination thereof. After completed collection the second embodiment of the capturing or collecting device is removed from the collector 4 of the ionizer 1 and is transferred to an analytical instrument, while in appropriate cases a new capturing or collecting device is inserted in the ionizer 1 and new particle collection is commenced either in the same or in a different location.

In order to improve even further the analytical work a third embodiment of the capturing or collecting device can be used—as is particularly evident from FIGS. 4A, 4B, 5A and 5B. This third embodiment comprises a first part 13, which is placed in electrical and mechanical contact, via its central portion 14, with the collector 4 of the ionizer 1 via its central recess 4a, and a second part 15 which has been given an essentially smaller active surface than the first part 13 and which may preferably have been treated in advance to react primarily or solely to a specific type of particle or substance when that type of particle or substance encounters its surface. One kind of such treatment is called that the second part 15 has been coated. By this means collection and detection of an extremely low concentration in the air of the specific type of particle or substance in question is made possible. The second part 15 is designed and constructed to advantage so that it fits exactly into and is adapted for the analytical instrument to be used, which may for example consist of an electronic microscope.

Variations of the invention are obviously possible within the scope of the appended claims.

The invention claimed is:

1. A device for collecting particles from a gas, said device comprising:
    an ionizer including at least one ion emitting unit which emits ions, and a collector for collecting particles from the gas that are charged by said ions; and
    an electrically conductive collecting device, which is electrically connected to the collector of said ionizers, and which is shaped substantially as a bowl;
    wherein the collected particles are subsequently analyzed in a particle analyzer.

2. A device as claimed in claim 1, wherein said collecting device is uncoverable.

3. A device as claimed in claim 1, wherein said collecting device is coverable with a lid.

4. A device as claimed in claim 1, wherein said collecting device is provided with a connection member for electrically connecting the collecting device to said collector.

5. A device as claimed in claim 1, wherein:
said collector is at least partly submerged in the ionizer so as to define a recess; and
said recess has a shape substantially corresponding to a shape of the collecting device.

6. A device as claimed in claim 1, wherein said collecting device comprises at least one grip that is adapted to be easily gripped while the collecting device is installed in the ionizer.

7. A device as claimed in claim 6, wherein the at least one grip comprises at least one of an edge and a lug.

8. A device as claimed in claim 1, wherein said collecting device includes an active collecting surface which is adapted in size and shape for use with said particle analyzer.

9. A device as claimed in claim 8, wherein said collecting surface, prior to use with said collector, is prepared in advance with at least one specific reagent.

10. A device as claimed in claim 8, wherein an active collecting surface of said collecting device is smaller than an active surface of the collector.

11. A device as claimed in claim 1, wherein said collecting device is made of an electrically conductive material.

12. A device as claimed in claim 1, wherein the at least one ion-emitting unit of said ionizer is directed away from said collecting device and is located at a long distance from said collecting device for the purpose of generating an electrostatic field therebetween, which will be as large as possible in relation to said long distance.

13. A device as claimed in claim 1, wherein said collecting device is detachable from the collector of the ionizer.

14. A device for collecting particles from a gas, said device comprising:
an ionizer including at least one ion emitting unit which emits ions, and a collector for collecting particles from the gas that are charged by said ions; and
an electrically conductive collecting device, which is electrically connected to the collector of said ionizer;
wherein the collected particles are subsequently analyzed in a particle analyzer; and
wherein the at least one ion-emitting unit comprises a plurality of prongs, which are spaced apart along a straight line, which protrude from said ionizer, and which are screened and protected in all directions except one direction which leads away from the ionizer by sleeves that are open at one end.

15. A device as claimed in claim 14, wherein said collecting device is shaped substantially as a bowl.

16. A device as claimed in claim 15, wherein said collecting device is coverable with a lid.

17. A device as claimed in claim 14, wherein said collecting device is coverable with a lid.

18. A device as claimed in claim 14, wherein said collecting device is provided with a connection member for electrically connecting the collecting device to said collector.

19. A device as claimed in claim 14, wherein:
said collector is at least partly submerged in the ionizer so as to define a recess; and
said recess has a shape substantially corresponding to a shape of the collecting device.

20. A device for collecting particles from a gas, said device comprising:
an ionizer including at least one ion emitting unit which emits ions, and a collector for collecting particles from the gas that are charged by said ions; and
an electrically conductive collecting devices which is electrically connected to the collector of said ionizer;
wherein the collected particles are subsequently analyzed in a particle analyzer; and
wherein the collecting device is made of an electrically conductive material which comprises extruded thermoplastic with an electrically conductive surface.

21. A device as claimed in claim 20, wherein said collecting device is provided with a connection member for electrically connecting the collecting device to said collector.

22. A device as claimed in claim 20, wherein:
said collector is at least partly submerged in the ionizer so as to define a recess; and
said recess has a shape substantially corresponding to a shape of the collecting device.

* * * * *